(12) United States Patent
Saleh et al.

(10) Patent No.: US 6,303,827 B1
(45) Date of Patent: Oct. 16, 2001

(54) PROCESS FOR MAKING AROMATIC ALDEHYDES

(75) Inventors: Ramzi Yanni Saleh, Baton Rouge, LA (US); Christopher L. Becker, Russell, KS (US); Robert C. Michaelson, Kinnelon; Richard H. Schlosberg, Bridgewater, both of NJ (US)

(73) Assignee: ExxonMobil Chemicals Patents Inc., Houston, TX (US)

( * ) Notice: Subject to any disclaimer, the term of this patent is extended or adjusted under 35 U.S.C. 154(b) by 0 days.

(21) Appl. No.: 09/393,664

(22) Filed: Sep. 10, 1999

Related U.S. Application Data

(60) Provisional application No. 60/099,783, filed on Sep. 10, 1998.

(51) Int. Cl.$^7$ .......................... C07C 45/00; C07C 51/16; C07C 63/14; C07C 65/00
(52) U.S. Cl. .......................... 568/428; 562/418; 562/480; 562/889
(58) Field of Search ............................ 568/428; 562/418, 562/480, 889

(56) References Cited

U.S. PATENT DOCUMENTS

| | | | |
|---|---|---|---|
| 2,485,237 | 10/1949 | Gresham et al. | 260/599 |
| 3,284,508 | 11/1966 | Gray et al. | 260/599 |
| 3,539,650 | 11/1970 | Amir . | |
| 3,644,552 | 2/1972 | Notaro et al. . | |
| 3,856,832 | 12/1974 | Ethyl Corp. | 260/410 |
| 3,948,998 | 4/1976 | Fujiyama et al. | 260/599 |
| 4,218,403 | 8/1980 | Vanderpool | 568/428 |
| 4,518,798 | 5/1985 | Kramer et al. | 560/233 |
| 4,554,383 | 11/1985 | Knifton | 568/428 |
| 5,453,538 | 9/1995 | Broeker et al. | 562/409 |
| 5,679,867 | 10/1997 | Bruce et al. | 568/428 |
| 5,910,613 * | 6/1999 | Schiraldi et al. | 568/428 |

FOREIGN PATENT DOCUMENTS

| | | |
|---|---|---|
| 502 333 | 7/1930 | (DE) . |
| 083224 * | 7/1983 | (EP) . |
| 896 960 | 2/1999 | (EP) . |
| 820545 | 11/1937 | (FR) . |
| 1108178 | 4/1968 | (GB) . |
| 2056979 | 3/1981 | (GB) . |
| 51-146430 | 12/1976 | (JP) . |
| WO 93/24432 | 12/1993 | (WO) . |

OTHER PUBLICATIONS

"Aldehyde Syntheses" G.A. Olah, et al., Friedel–Crafts and Related Reactions, Wiley–Interscience, vol. III, Chapter XXXVIII, pp. 1153–1256, 1964.

"Superacid–Catalyzed Formylation of Aromatics with Carbon Monoxides," G.A. Olah et al., J. Org. Chem., vol. 50, pp. 1483–1486, 1985.

"Aromatic Substitution, XXXIX$^1$ Varying Selectivity in Electrophilic Formylation of Toluene and Benzene" G.A. Olah, et al., J. Am. Chem. Soc., vol. 98, 1, pp. 296–297, Jan. 7, 1976.

* cited by examiner

Primary Examiner—Johann Richter
Assistant Examiner—J. Parsa
(74) Attorney, Agent, or Firm—Paul T. LaVoie

(57) ABSTRACT

Alkyl aromatic compounds are converted to alkyl aromatic aldehydes by a carbonylation reaction. The carbonylation catalyst can be a high boiling point carbonylation catalyst which allows for the separation of the aldehyde product by selective volatilization. Alternatively, the carbonylation catalyst can be selected from perfluoroalkyl sulfonic acids having 2 to 18 carbon atoms, perfluoroether sulfonic acids having 2 to 18 carbon atoms, $BF_3(ROH)_x$ wherein R represents $CH_3$ or H and X is a number within the range of from 0.2 to 2, $GaBr_3$, $GaCl_3$, $TaF_5$, $NbF_5$, and $NbBr_5$, with the proviso that when the catalyst is $TaF_5$, $NbF_5$, or $NbBr_5$, then the reaction takes place in the absence of added HF. Preferably, all of the carbonylation reactions take place in the absence of added HF. The alkyl aromatic aldehydes can be oxidized to form an aromatic acid. A mixed xylene feed stock can be converted to a mixture of dimethylbenzaldehydes and then oxidized to form trimellitic acid without the need to separate the xylene or dimethylbenzaldehyde isomers.

31 Claims, No Drawings

PROCESS FOR MAKING AROMATIC ALDEHYDES

This application is Provisional of 60/099,783 filed on Sep. 10, 1998.

BACKGROUND OF THE INVENTION

1. Field of the Invention

The present invention relates to a process for making alkyl aromatic aldehydes and aromatic acids from alkyl aromatic compounds and to catalysts useful therein.

2. Description of the Related Art

Carbonylation of an alkyl aromatic compound to form an aldehyde can be carried out by a reaction generally referred to as the Gatterman-Koch reaction. Published in 1897, Gatterman and Koch described the direct carbonylation of various aromatic compounds by the use of carbon monoxide and hydrogen chloride in the presence of aluminum chloride and cuprous chloride (Gatterman, L. and Koch, J. A., Chem. Ber., 30, 1622 (1897)). The reaction was subsequently expanded to include other Lewis acids. Further, it was discovered that the cuprous chloride could be eliminated if the CO pressure was increased. A review of such reactions is set forth in Olah, G. A., "Friedel-Crafts and Related Reactions", Wiley-Interscience, N.Y., Vol. III, 1153 (1964).

U.S. Pat. No. 2,485,237, for example, describes replacing the hydrogen chloride and aluminum chloride catalyst combination with hydrogen fluoride and boron trifluoride. Further use of the HF—$BF_3$ catalyst is described in U.S. Pat. No. 3,284,508 where the recovery of the fluorides is stated to be improved.

The HF—$BF_3$ catalyst combination is sometimes modified to a two step process where a toluene—HF—$BF_3$ complex is preformed and reacted with CO to form tolualdehyde. Afterward, make-up CO and optionally additional toluene are added to the reaction medium. An example of such a process is set forth in U.S. Pat. No. 3,948,998.

Other catalysts that have been reported for use in a Gatterman-Koch type carbonylation reaction include combinations of Lewis and strong Bronsted acids such as $SbF_5$—HF as is described in U.S. Pat. No. 4,218,403. The use of Bronsted superacids alone, such as fluorosulfonic acid or trifluoromethane sulfonic acid, were also reported to be effective catalysts. See for example Olah, G. A., Laali, K., and Farooq, O., J. Org. Chem., 50, 1483 (1985).

However, the catalysts used in a Gatterman-Koch carbonylation reaction are typically complexed with the aldehyde product. Thus, a stoichiometric amount of catalyst is "consumed" in the reaction. Further, in order to obtain the aldehyde product in a complex-free form, a separation step is needed. For instance, water can be added to a tolualdehyde—$AlCl_3$ complex to obtain the aldehyde product in a complex-free form. However, this step also chemically alters and destroys the utility of the catalyst. Such a separation, which leads to a one time use of catalyst renders this process commercially unattractive as catalyst regeneration and recycle would be prohibitively expensive.

A method that includes catalyst recycling is proposed by Olah, G. A. et al., J. Am. Chem. Soc., 98:1, 296 (1976). Here, a modified Gatterman-Koch reaction that employs $BF_3$—HF as a catalyst complex is used to form the aldehyde. The reaction is carried out at low temperatures, typically from 0–20° C., and with excess HF. The catalyst is separated from the aldehyde-catalyst complex by a distillation technique wherein the $BF_3$ and HF are boiled off, condensed and returned to the carbonylation reactor.

While this method is useful, it is generally desirable to have a method that avoids the use of HF, a material which requires special containment and handling facilities. Also, it would be desirable to provide an alternate method for separating the aldehyde from the catalyst.

SUMMARY OF THE INVENTION

The present invention relates to a process for forming alkyl aromatic aldehydes using novel reaction or separation conditions in a Gatterman-Koch reaction and to the optional oxidation of the aldehydes to form aromatic acids and anhydrides. More specifically, one aspect of the present invention provides a process that comprises (a) reacting an alkyl aromatic compound with carbon monoxide in the presence of a high boiling point carbonylation catalyst to form an alkyl aromatic aldehyde and (b) separating the alkyl aromatic aldehyde from the carbonylation catalyst by selectively volatilizing the alkyl aromatic aldehyde. Because the carbonylation catalyst has a high boiling point, the alkyl aromatic aldehyde can be boiled off, thereby disengaging the aldehyde from the aldehyde-catalyst complex. The catalyst can be recycled to the carbonylation reaction or reused in a subsequent carbonylation reaction. To avoid undesired degradation and side reactions, the selective volatilization is preferably carried out quickly at high temperatures and/or reduced pressures.

A second aspect of the invention provides a process that comprises reacting an alkyl aromatic compound with carbon monoxide in the presence of a carbonylation catalyst selected from the group consisting of perfluoroalkyl sulfonic acids having 2 to 18 carbon atoms, perfluoroether sulfonic acids having 4 to 18 carbon atoms, $GaBr_3$, $GaCl_3$, $TaF_5$, $NbF_5$, $NbBr_5$, and $BF_3 \cdot (ROH)_x$ wherein R represents $CH_3$ or H and X is a number from 0.2 to 2, to form an alkyl aromatic aldehyde, with the proviso that when the catalyst is $TaF_5$, $NbF_5$, or $NbBr_5$, then said reaction takes place in the absence of added HF. For convenience, it is preferable that all of the catalysts in this embodiment are used in the absence of added HF, and more preferably all of the catalyst in all embodiments of the invention are used in the absence of added HF.

The alkyl aromatic compounds are typically toluene or xylenes, although other aromatics are also suitable, which are converted to p-tolualdehyde and dimethyl benzaldehydes, respectively. A further application of the invention is to subject the isolated aldehydes to oxidation to produce an aromatic acid or, after dehydration, an anhydride. For example, p-tolualdehyde can be oxidized to terephthalic acid, a commonly used monomer in the production of commercial polyesters. Similarly, dimethyl benzaldehyde can be oxidized to obtain trimellitic acid and subsequently dehydrated to trimellitic anhydride. This also relates to a third aspect of the present invention which involves (a) reacting a mixture of ortho-, meta-, and para-xylenes with CO in the presence of a carbonylation catalyst to form a mixture of dimethylbenzaldehydes; (b) oxidizing the mixture of dimethylbenzaldehydes to form trimellitic acid; and (c) dehydrating the trimellitic acid to form trimellitic anhydride. In this way, trimellitic anhydride can be made from a mixed xylene feed. Thus, the present invention can also provide a convenient and economical route to the production of these and other valuable aromatic acid compounds.

Another application of the present invention is to reactively separate xylene isomers by carbonylation. This fourth aspect of the invention relates to separating para-xylene from a mixture of xylenes by reacting a mixture of ortho-, meta-, and para-xylenes with CO in the presence of a carbonylation catalyst to convert substantially all of the ortho- and meta-xylenes to dimethylbenzaldehydes and then isolating the unreacted para-xylene.

DETAILED DESCRIPTION OF THE INVENTION

Many carbonylation catalysts are already known in the art. For purposes of the present invention, a "carbonylation catalyst" is any compound, mixture of compounds or element that can catalyze the reaction of an alkyl aromatic compound with CO to form an alkyl aromatic aldehyde. Generally, carbonylation catalysts are Lewis and/or Bronsted acids. "High boiling point carbonylation catalyst" means a catalyst as just described that has a boiling point that is higher than the targeted aromatic aldehyde to be produced. Typically, the high boiling point carbonylation catalyst has a boiling point of at least 210° C., preferably at least 230° C., and more preferably at least 250° C. The catalyst can be in liquid or solid form, the latter including supported and unsupported catalysts. Suitable support materials are, in general, well known in the catalyst art and include zeolites, ceramics and polymeric supports. Specific examples include aluminas and siliceous materials. For purposes of this invention, a high boiling point carbonylation catalyst includes solid and supported catalysts that do not boil per se, but rather melt, degrade, etc. at high temperatures. These types of catalysts are deemed to have a boiling point above their melting/degrading temperature. So long as the aldehyde product can be boiled off, that is volatilized, and thus separated from the carbonylation catalyst, the solid or supported catalyst is within the scope of a high boiling point carbonylation catalyst.

Specific carbonylation catalysts that are contemplated for use in the present invention include the following: perfluoroalkyl sulfonic acids having 2 to 18 carbon atoms, perfluoroether sulfonic acids having 2 to 18 carbon atoms, $GaBr_3$, $GaCl_3$, $AlBr_3$, $AlCl_3$, $AlI_3$, $TaF_5$, $NbF_5$, $NbBr_5$ and $BF_3 \cdot (ROH)_x$ wherein R represents $CH_3$ or H and X is a number from 0.2 to 2.0. All of these catalysts, except $BF_3 \cdot (ROH)_x$, are high boiling point carbonylation catalysts.

The perfluoroalkyl sulfonic acids include compounds of the formula $R_fSO_3H$ wherein $R_f$ is a straight or branched chain perfluoroalkyl group having 2 to 18 carbon atoms, preferably 2 to 8 carbon atoms. Examples of such carbonylation catalysts include perfluoroethane sulfonic acid, perfluorobutane sulfonic acid, perfluorohexane sulfonic acid and perfluorooctane sulfonic acid.

The perfluoroether sulfonic acids are typically of the formula $R^1_fOR^2_fSO_3H$ wherein $R^1_f$ and $R^2_f$ each independently represent a straight or branched chain perfluoroalkyl group having 1 to 10 carbon atoms, preferably 1 to 4 carbon atoms. Acids of this type include compounds of the formula $CF_3(CF_2)_zO(CF_2)_ySO_3H$ wherein Z and Y are each independently a number from 1 to 3. An example of a perfluoroether sulfonic acid carbonylation catalyst is perfluoroethoxyethane sulfonic acid.

It should be understood that the carbonylation catalyst compounds described herein are used with their conventional meanings and thus include all variations of the compounds, including ionic and complexed forms, as may occur in situ. For example, in the presence of protons, the Lewis acid $AlCl_3$ is believed to form $H^+$ and $AlCl_4^-$. Further, the $AlCl_4^-$ can combine with $AlCl_3$ to form $Al_2Cl_7^-$ and higher homologues. Recognizing that in situ changes can occur to the "catalyst" compound as supplied, including complexing reactions or rearrangements that improve the catalytic activity, all such forms and variations are collectively embraced by reference to the compound supplied to the reaction system. Thus, for example, identifying the catalyst as $AlCl_3$ embraces carrying out the carbonylation reaction in the presence of any of $AlCl_3$, $AlCl_4^-$, $Al_2Cl_7^-$ and/or higher homologues thereof.

In general, it is preferred that the reaction is carried out in the absence of any added HF. This means that no effort is taken to add HF to the reaction system. However, HF may be present in the feeds as an impurity. Similarly, HF may be created in situ when a fluoride-containing compound is present. Such in situ formation does not correspond to "added HF."

A second aspect of the present invention relates to the use of specified carbonylation catalysts that have been discovered to be suitable in the carbonylation of alkyl aromatic compounds. Specifically, a process which comprises reacting an alkyl aromatic compound with carbon monoxide in the presence of a carbonylation catalyst selected from the group consisting of perfluoroalkyl sulfonic acids having 2 to 18 carbon atoms, perfluoroether sulfonic acids having 2 to 18 carbon atoms, $GaBr_3$, $GaCl_3$, $TaF_5$, $NbF_5$, $NbBr_5$, and $BF_3 \cdot (ROH)_x$ wherein R represents $CH_3$ or H and X is a number within the range of from 0.2 to 2, to form an alkyl aromatic aldehyde, with the proviso that when the catalyst is $TaF_5$, $NbF_5$, or $NbBr_5$, then said reaction takes place in the absence of added HF, Preferably the reaction with any of the carbonylation catalysts is carried out in the absence of added HF. In this embodiment of the invention, the separation technique used to isolate the aldehyde product is not particularly limited and need not be by selective volatilization.

The alkyl aromatic compounds to be treated in the present invention are hydrocarbon aromatic ring compounds having one or more $C_1$–$C_4$ alkyl substituents. Generally the alkyl aromatic compounds are substituted benzenes or naphthalenes having 1 to 3 alkyl groups, preferably methyl groups, directly bonded to the ring. Examples of alkyl aromatic compounds include toluene, o-, m-, p-xylenes, pseudocumene (1,2,4-trimethylbenzene), mesitylene (1,3,5-trimethylbenzene), propylbenzene, isopropylbenzene, and methylnaphthalene.

The alkyl aromatic compound is converted to the corresponding aldehyde as a result of the carbonylation reaction. The formyl group is directly bonded to the ring. For toluene, the reaction can be represented as follows:

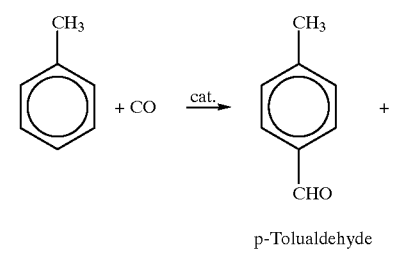

p-Tolualdehyde

-continued

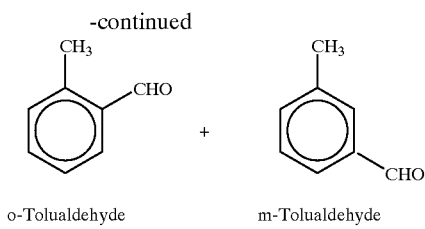

o-Tolualdehyde  +  m-Tolualdehyde

The reaction produces p-tolualdehyde with high selectivity, generally greater than 85%, depending upon the catalyst, the reaction temperature, and reaction pressure. The o-tolualdehyde is the next most abundant product and is generally produced in amounts of less than 10% (8–10%). The m-tolualdehyde is the least produced of the isomers at less than 2%.

Similarly, the carbonylation of xylenes can be represented as follows:

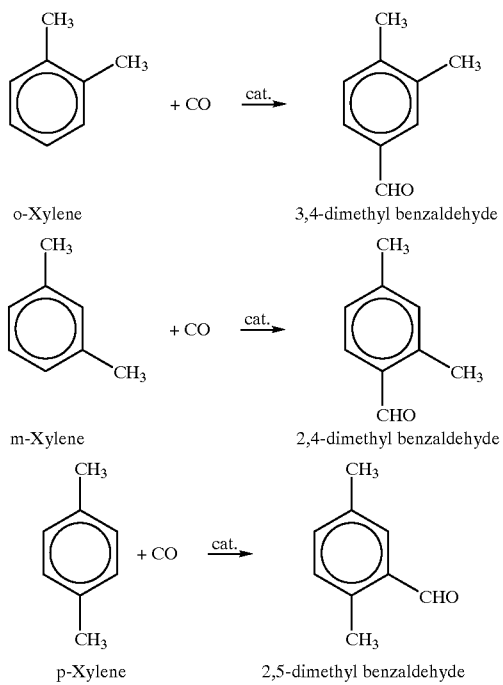

o-Xylene → 3,4-dimethyl benzaldehyde m-Xylene → 2,4-dimethyl benzaldehyde p-Xylene → 2,5-dimethyl benzaldehyde The most reactive is m-xylene to produce 2,4-dimethylbenzaldehyde. Although all three xylene isomers can be converted to the corresponding benzaldehyde, the difference in conversion rates can also be used to separate p-xylene from m- and o-xylenes. That is, the carbonylation reaction can be structured so that the faster reacting m- and o-xylenes are substantially converted to dimethylbenzaldehydes while the p-xylene is substantially not converted. Generally, these conditions include higher catalyst loading, higher temperatures, and/or longer reaction times so as to improve the overall conversion rates. The conditions should cause sufficient conversion of ortho-xylene, whereby the same or higher conversion of the more reactive meta-xylene will also occur. Separating the dimethylbenzaldehydes from the remaining, unreacted p-xylene such as by distillation or fractionation is easier than separating m- and o-xylenes from p-xylene. Similarly, ethylbenzene which is commonly found in xylene feeds has low carbonylation yields. While carbonylation can be accomplished, the lower reaction rate can be used to separate xylenes from ethylbenzene in a similar manner as the separation of m- and o-xylenes from p-xylene. This also means that ethylbenzene does not have to be removed from the alkyl aromatic compound feedstock before carbonylation occurs. Instead, the reaction conditions can take advantage of the differences in reactivity to selectively produce the targeted aldehyde, here dimethylbenzaldehyde.

Similarly, pseudocumene can be carbonylated to 2,4,5-trimethylbenzaldehyde and mesitylene can be carbonylated to mesitaldehyde.

All of the reactants and catalysts are readily available, commercially attainable or can be made by general methods or techniques known to workers skilled in the art from known or readily available starting materials.

The carbonylation reaction is typically carried out by combining the catalyst, optionally a solvent, and the alkyl aromatic compound in a reactor and adding carbon monoxide gas thereto. The catalyst can be combined or dissolved with the alkyl aromatic compound to form a solution or a slurry; i.e., the latter is formed if a solid carbonylation catalyst is used, either as a premix that is added to the reactor or formed in situ. The reaction can be carried out in either batch or continuous fashion. The amount of catalyst is not particularly limited and is generally equal to at least one half of the molar amount of alkyl aromatic compound, typically from 0.5 to 20 times the amount of alkyl aromatic compound. For a Bronsted acid catalyst such as the perfluoroalkyl sulfonic acids, it is preferred that the catalyst be provided in molar excess to the alkyl aromatic compound, preferably from 6 to 20, more usually from 6 to 12 moles of acid catalyst for each mole of alkyl aromatic compound. In general, higher Bronsted acid catalyst concentrations provide for higher conversion. For a Lewis acid catalyst such as aluminum halides and gallium halides, it is preferred that the catalyst be provided in an amount of 0.8 to 1.5 times the amount of alkyl aromatic compound and generally around or slightly in excess of a 1:1 ratio relative to the alkyl aromatic compound.

The reaction is generally carried out at a pressure from about atmospheric to superatmospheric pressure. More concretely, the reaction pressure is typically from about 0 to 300 $kg/cm^2$ (gauge), more typically from about 15 to 200 $kg/cm^2$ (gauge). In some embodiments, the reaction pressure is superatmospheric and is at least 4 $kg/cm^2$ (gauge), and preferably in the range from 4 to 100 $kg/cm^2$ (gauge), more preferably from 4 to 25 $kg/cm^2$ (gauge). Of course, an increase in pressure generally increases the cost of the reaction and/or the equipment and must be balanced against the increased productivity, if any. The use of a lower reaction pressure can be facilitated by incorporating copper or silver compounds into the reaction mixture. Specifically, cuprous chloride, as was used in the original Gatterman-Koch reaction, copper oxide or silver oxide, as are described in U.S. Pat. No. 4,518,798, can each be used to improve the conversion rate at lower reaction pressures and/or more mild overall reaction conditions. Other metal salts, as is known in the carbonylation art, can be also used.

The reaction pressure can be entirely from CO or from a CO containing gas. The co-presence of $CO_2$ or $H_2$ in the CO gas supplied to the reactor does not normally affect the carbonylation reaction. Accordingly, synthesis gas, which is comprised of CO, $H_2$, and optionally $CO_2$ in varying proportions, may be supplied to the reactor without the need to isolate or purify the CO therefrom. The amount of CO supplied is generally in excess of the amount needed. The pressure or partial pressure provided by CO is referred to herein as the "carbon monoxide gas pressure" and is generally from 0 to 200 kg/cm$^2$ (gauge), more typically from 1 to 100 kg/cm$^2$ (gauge), and preferably from 2 to 25 kg/cm$^2$ (gauge). The amount of CO is generally at least 20 mol % of the gas supplied. For example, synthesis gas can vary from a CO:H$_2$ ratio of 1:1 to 1:3. Further CO$_2$ can also be present in amounts of up to 30 mol %. Of course, the gas supplied to the reactor can be 100% CO.

The reaction can be carried out over a wide range of temperatures and is not particularly limited. Usually the reaction temperature is within the range of from 0° C. to 175° C., more typically within the range of from 0° C. to 100° C. such as from 0° C. to 50° C. However, surprisingly with regard to the BF$_3$·(ROH)$_x$ catalyst, a higher than usual temperature is preferred. For example, a temperature from 50° C. to 200° C., more preferably from 60° C. to 125° C., provides for better conversion and selectivity to the desired product.

The carbonylation reaction is carried out for a sufficient time to achieve the desired product or conversion under the conditions employed. Generally the reaction is run for 0.1 to 5 hours although longer or shorter times can be used.

After the reaction, the aromatic aldehyde-catalyst complex can be broken and the aldehyde isolated from the reaction medium by a variety of methods known in the art, including quenching with water and liquid extraction. When a high boiling point carbonylation catalyst is used, the separation is preferably conducted by selectively volatilizing the aldehyde product. Surprisingly, the aldehyde product is susceptible to being volated without substantial degradation. The volatilization technique employed should be effective in achieving separation in a short time period in order to avoid unwanted side reactions, degradation, etc, that are prone to occur in heating the aldehyde and acid-containing liquid phase. Generally, the volatilization technique has a liquid residence time of less than 5 minutes, preferably less than 3 minutes, more preferably less than 1 minute. Suitable techniques include evaporation, vaporization, flash distillation and combinations thereof. As is well understood, increasing the temperature and/or decreasing the pressure will favor volatilization. In general, the temperature reaches at least 90° C. and typically is within the range from 100° C. to 350° C.

The term "selectively volatilizing" means that the volatilizing technique is intended to convert the desired product, the aldehyde, and not the undesired product, the carbonylation catalyst, into a vapor thereby separating the two components. However, a perfect split is generally not possible or practical. Indeed, so long as the catalyst has some vapor pressure, the aldehyde-rich vapor phase will contain some amount of catalyst. Accordingly, for purposes of the present invention, the separation is considered to be selective for the aldehyde product if less than 50% of the acid catalyst, preferably less than 30%, and more preferably less than 15%, of the acid catalyst is present in the resulting aldehyde-rich vapor phase.

In one embodiment, a wiped-film evaporator, sometimes referred to as an agitated-film evaporator, is used. These units are generally comprised of a straight or tapered tube having a concentric, rotating paddles arranged therein. The edge of the paddles can be in or above the film layer. Liquid is run down the interior surface of the tube as a thin film. The paddles are rotated to aid in the formation of the desired film thickness. The wall is normally heated. In use, the volatile material is volatized forming a vapor phase in the annular region of the tube and removed as vapor. The process can be run at a variety of pressures, but is preferably carried out under reduced pressure or vacuum. The wall temperature is typically at least 90° C., and is usually in the range of 100° C. to 300° C. It should be noted that the lower temperatures, i.e. those less than 200° C., are nonetheless sufficient to volatilize the aldehyde provided the pressure is sufficiently low. To increase the separation efficiency, regardless of the temperature, it is preferred that the pressure is less than or equal to 0.5 kg/cm$^2$, more preferably less than 0.1 kg/cm$^2$. The condensate contains the aldehyde product and any unreacted alkyl aromatic compound while the liquid film contains all or substantially all of the carbonylation catalyst which can optionally be recycled to the carbonylation reactor.

In another embodiment, a flash distillation unit is used. Here the liquid and optionally the gas phase(s) from the carbonylation reactor can be sent to the flash chamber where the more volatile aldehyde product is flashed off by well known techniques and conditions. The catalyst substantially remains in the liquid phase and exits as bottoms, optionally to be recycled to the carbonylation reactor. The overhead or distillate contains the aldehyde product and the unreacted alkyl aromatic compound, if any. As mentioned above, it is preferred that the heating of the aldehyde-containing liquid occur rapidly and that the duration of the aldehyde in the presence of the catalyst in the liquid phase under heated conditions be minimized so as to avoid degradation reactions. One way of achieving this is to heat the liquid phase in a heat exchanger very quickly just prior to introducing the liquid into the flash chamber. The temperature is preferably increased to at least 200° C., more preferably within the range from 230° C.–300° C., in less than 4 minutes, preferably less than 2 minutes, more preferably in less than 20 seconds. The rapidly heated liquid can then be supplied to the flash chamber where the more volatile components such as the aldehyde product can be rapidly flashed off. Under this technique, the aldehyde will generally start to vaporize in the heat exchanger before reaching the flash chamber, thereby reducing the average aldehyde-acid contact time under heated conditions. Conveniently, the carbonylation reactor pressure, when superatmospheric, can be used to drive the product through the heat exchanger or heat exchangers and, even with a pressure drop across the heat exchanger, to facilitate a significant pressure drop in the flash chamber. The residence time in the flash chamber is typically very low such as 10 seconds or less, preferably 5 seconds or less, for the liquid and generally 5 seconds or less, preferably 2 seconds or less for the gas.

After the flash, the vapor phase is preferably subjected to an absorbing tower or other suitable unit to remove any carbonylation catalyst that is present in the vapor phase. For example, the vapor can be run through a multiplate column where a diluent such as toluene is added counter currently. The carbonylation catalyst, if any, will re-complex with the aldehyde and rapidly condense out of the vapor. This leaves a vapor stream of aldehyde and excess diluent and/or aromatic alkyl compound with essentially no carbonylation catalyst. The liquid stream containing the aldehyde-catalyst complex can be recycled back to the heat exchanger and flash chamber. Such an absorbing column is preferably used with the flash separation technique, but is suitable for use with any selective volatilization method.

After separation, the alkyl aromatic aldehydes can preferably be subjected to an oxidation reaction to form the corresponding aromatic acids and optionally dehydrated to the anhydrides thereof. The reaction conditions and catalysts for such an oxidation reaction are, in general, well known in the art. In general, oxidation comprises combining the aromatic aldehyde compound with molecular oxygen, optionally in the presence of an oxidation catalyst. The reaction usually takes place in a solvent for the reaction such as a lower aliphatic acid, an ester or water. Examples of solvents include formic acid, acetic acid, propionic acid, n-butyric acid, iso-butyric acid, valeric acid, trimethylacetic acid, caproic acid, methyl benzoate, dimethyl terephthalate and water. The oxidation catalysts are well known and include cobalt salts, manganese salts, chromium salts, lanthanide salts especially cerium salts, and mixtures thereof. Examples of catalysts include Co(II) acetate or naphthenate, and manganese (II) acetate or naphthenate. A combination of Co/Mn is particularly preferred as a catalyst. The amount of catalyst is not particularly limited and is generally within the range from 50 to 1000 ppm for Mn and 50 to 2000 ppm for Co, based on the solvent. Bromine or other free radical initiators may optionally be included to aide in the reaction as is well known in the art. However, because the oxidation is carried out on an aldehyde compound, free radical initiators such as HBr can be advantageously minimized or omitted. Further, in view of its corrosive nature, bromine, or a progenitor thereof, is preferably excluded from the oxidation reaction or minimized as is described in U.S. Pat. No. 5,453,538.

The molecular oxygen used in the oxidation reaction can be supplied to the reactor as pure oxygen or as a mixed gas containing other inert gases such as nitrogen. Thus, air can be used as the feed or source of molecular oxygen. The oxidation reaction is preferably conducted at a pressure that will maintain a substantial liquid phase of aromatic acid compound and about 70% to 80% of the reaction solvent. Typically the oxidation reaction pressure is from 0 to 35 kg/cm² (gauge), more preferably from 10 to 30 kg/cm² (gauge). The oxidation reaction temperature is generally within the range from 100° C. to 252° C., more typically 120° C. to 240° C.

One of the preferred embodiments involving the subsequent oxidation reaction is the conversion of p-tolualdehyde to terephthalic acid as shown below:

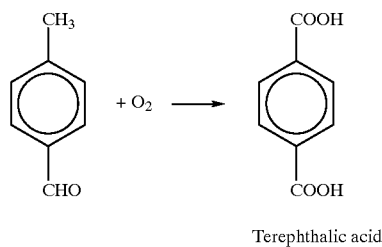

Terephthalic acid

By this method, toluene can be used as a starting material for producing terephthalic acid.

Another preferred embodiment is the oxidation of the dimethyl benzaldehydes produced from the carbonylation of xylenes to form trimellitic acid which can be dehydrated to form trimellitic anhydride having the formula:

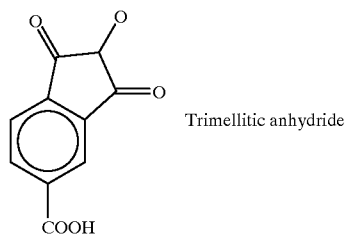

Trimellitic anhydride

The trimellitic anhydride can be produced from any of the dimethyl benzaldehyde isomers produced from carbonylation of xylenes. This represents another embodiment of the present invention wherein a xylene feed that contains ortho-, meta-, and para-xylene can be reacted with CO in the presence of a carbonylation catalyst and the resulting mixture of dimethylbenzaldehyde isomers can be subjected to oxidation to produce trimellitic acid without the need to isolate a particular isomer of either the xylene feed or the dimethylbenzaldehyde products. This result is not carbonylation catalyst dependent and thus can be achieved using any carbonylation catalyst.

The other alkyl aromatic aldehydes can also be oxidized to form a corresponding aromatic acid. For example, 2,4,5-trimethylbenzaldehyde, which can be obtained by carbonylating pseudocumene, can be oxidized to form pyromellitic acid and after dehydration pyromellitic dianhydride. Likewise, mesitaldehyde can be oxidized to form trimethyl benzoic acid.

The following non-limiting examples are provided in order to further demonstrate the various embodiments and advantages of some forms of the present invention.

EXAMPLE 1

Perfluorooctanesulfonic acid (8 grams) and toluene (3 mL) were charged to a Hastelloy C minireactor tube equipped with two valves. The reactor was pressurized with CO to 1050 psig, sealed, placed in a shaker-mounted heated block, and shaken at 500° C. for two hours. The reactor was quickly cooled to room temperature and vented. The contents were poured into ice water, and the organic layer was extracted with diethyl ether. Analysis by gas chromatography showed about 1% conversion of the toluene. The product isomer distribution was 93% para-tolualdehyde, 7% ortho-tolualdehyde, and no meta-tolualdehyde.

EXAMPLE 2

Perfluorohexanesulfonic acid (6 grams) and toluene (3 mL) were charged to the reactor. The rest of the procedure was the same as in Example 1. Analysis by gas chromatography showed about 2% conversion of the toluene. The product isomer distribution was again 93% para-tolualdehyde, 7% ortho-tolualdehyde, and no meta-tolualdehyde.

EXAMPLE 3

Perfluoroethoxyethanesulfonic acid (7 grams) and toluene (3 mL) were charged to the reactor. The rest of the procedure was the same as in Example 1, except the reactor was not heated. Analysis by gas chromatography showed about 9% conversion of the toluene. The product isomer distribution was again 93% para-tolualdehyde, 7% ortho-tolualdehyde, and no meta-tolualdehyde.

EXAMPLE 4 (reference)

Trifluoroacetic acid (7 grams) and toluene (3 mL) were charged to the reactor. The rest of the procedure was the same as in Example 1, except the reactor was not heated. No product aldehydes were found.

EXAMPLE 5

This Example demonstrates separation of the acid catalyst from the aldehyde product. The complex of perfluorohexanesulfonic acid with para-tolualdehyde. (26 grams) was dissolved in trifluoroacetic acid (53 grams). This solution was fed to a wiped-film evaporator apparatus over a period of 20 minutes. The evaporator was run with a wall temperature of 100° C. under a vacuum of 0.25 mmHg. The material that collected on the cold finger of the evaporator was analyzed by gas chromatography and found to be para-tolualdehyde. The perfluorohexanesulfonic acid was non-volatile (boiling point 260° C.) and was collected at the bottom of the evaporator, while the trifluoroacetic acid solvent volatilized and was collected in a dry ice trap.

EXAMPLE 6 (reference)

This Example demonstrates that the trifluoromethanesulfonic (triflic) acid catalyst cannot be selectively separated from the para-tolualdehyde product by volatilization. Rather, para-tolualdehyde degradation results when using an acid with a higher vapor pressure than the para-tolualdehyde.

The liquid complex of trifluoromethanesulfonic acid with para-tolualdehyde (130 grams) was fed to a wiped-film evaporator apparatus over a period of 40 minutes. The evaporator was run with a wall temperature of 115° C. under a vacuum of 0.4 mmHg. The material that collected on the cold finger of the evaporator (about 105 grams) was identified as trifluoromethanesulfonic acid. The non-volatile fraction was collected at the bottom of the evaporator as a dark black, viscous liquid that was very soluble in toluene. GC analysis of this heavy fraction showed mainly higher boiling products, and no para-tolualdehyde.

EXAMPLE 7

In a manner similar to Example 1, toluene and $GaBr_3$ were supplied to a minireactor to form a reaction mixture having a ratio of 0.2 mol $GaBr_3$/mol toluene. The reactor was pressurized with CO to 1100 psig and run for one hour at room temperature. Analysis showed about 20% conversion of the toluene. The product isomer distribution was 91% para-tolualdehyde, 8% ortho-tolualdehyde, and 1 meta-tolualdehyde.

EXAMPLE 8

In a manner similar to Example 1, mixed xylenes (32.5% para, 32.5 meta, 35% ortho) and $GaBr_3$ were supplied to a minireactor to form a reaction mixture having a ratio of 0.2 mol $GaBr_3$/mol xylenes. The reactor was pressurized with CO to 1100 psig and run for one hour at room temperature. Analysis showed about 22% conversion of the xylenes. The product isomer distribution was 21.2% 3,4-dimethylbenzaldehyde, 74.8% 2,4-dimethylbenzaldehyde, and 4.1% 2,5-dimethylbenzaldehyde.

EXAMPLE 9

In a manner similar to Example 1, toluene and $TaF_5$ were supplied to a minireactor to form a reaction mixture having a ratio of 0.2 mol $TaF_5$/mol toluene. The reactor was pressurized with CO to 950 psig and run for 3.5 hours at room temperature. Analysis showed about 1% conversion of the toluene.

EXAMPLE 10

In a manner similar to Example 1, toluene and $NbF_5$ were supplied to a minireactor to form a reaction mixture having a ratio of 0.2 mol $NbF_5$/mol toluene. The reactor was pressurized with CO to 1050 psig and run for 2.0 hours at room temperature. Analysis showed conversion of the toluene at less than 1%.

EXAMPLE 11

In a manner similar to Example 1, toluene and $NbBr_5$ were supplied to a minireactor to form a reaction mixture having a ratio of 0.2 mol $NbBr_5$/mol toluene. The reactor was pressurized with CO to 1050 psig and run for 2.0 hours at room temperature. Analysis showed conversion of the toluene at less than 1%.

EXAMPLE 12

$GaCl_3$ and toluene were charged to a 500 cc stirred autoclave in a $GaCl_3$:toluene molar ratio of 0.16. The reaction was run at varying CO pressures and temperatures and samples were withdrawn at various times and analyzed. After 3.09 hours at a temperature of 25° C.–26° C. and under a CO pressure of 1068–1077 psig, 15.6% of the toluene had been converted to tolualdehyde. The product isomer distribution was 88.8% para-tolualdehyde, 10.3% ortho-tolualdehyde, and 0.9 meta-tolualdehyde. The CO pressure was then increased to the range of around 1536 to 1549 psig and measurements at 7.08 hours from start showed 16.9% conversion. The product isomer distribution was 88.2% para-tolualdehyde, 10.7% orthotolualdehyde, and 1.1% meta-tolualdehyde.

EXAMPLE 13

A $BF_3$·monomethanol catalyst was prepared in situ at 20–40° C. in a 150 cc Hastelloy C autoclave. The reactor was pressurized with 1200 psig CO at a temperature of 75° C. Meta-xylene was added slowly with a final catalyst:xylene ratio of 5:1 (g:g). The total elapsed time for the reaction was 90 minutes at which point the reactor was cooled to room temperature. At room temperature, the CO overpressure was vented and the remaining gaseous CO and $BF_3$ were purged with nitrogen. The autoclave contents were drained into a separatory funnel, 110 grams of methanol (excess) was added and the mixture extracted twice with 50 cc of octane. The combined octane extracts were shown by I. R. and GC/MS to contain aromatic aldehyde. IR: C=O at 1703 $cm^{-1}$, C—H at 2732 $cm^{-1}$·GC/MS showed a peak whose mass spectrum is consistent with that of 2,4-dimethylbenzaldehyde.

EXAMPLE 14

Example 13 was essentially repeated only using a $BF_3$·water catalyst. After the reaction, CO and $BF_3$ gases were stripped and the reactor contents drained into a 300 cc Hoke bomb. The mixture was then added to enough water to make $BF_3$·dihydrate, the aqueous phase was extracted twice with diethyl ether and the mixture extracted twice more with octane. IR: C=O at 1703 $cm^{-1}$, C—H at 2732 $cm^{-1}$. GC/MS showed a peak whose mass spectrum is consistent with that of 2,4dimethylbenzaldehyde.

The present application claims the benefit of priority under 35 U.S.C. § 119 from U.S. application No. 60/099,783 filed Sep. 10, 1998, the entire contents of which are incorporated herein by reference. The invention having been thus described, it will be obvious that the same may be varied in many ways without departing from the spirit and scope of the invention as defined by the following claims.

We claim:

1. A process, which comprises the steps of:
   (a) reacting an alkyl aromatic compound with carbon monoxide in the presence of a high boiling point carbonylation catalyst to form an alkyl aromatic aldehyde, wherein the catalyst has a first boiling point higher than a second boiling point of the aldehyde; and
   (b) separating said alkyl aromatic aldehyde from said carbonylation catalyst by selectively volatilizing said alkyl aromatic aldehyde at a temperature greater than 200° C.

2. The process according to claim 1, wherein said high boiling point carbonylation catalyst has a boiling point higher than 210° C.

3. The process according to claim 2, wherein said high boiling point carbonylation catalyst has a boiling point higher than 250° C.

4. A process, which comprises the steps of:
   (a) reacting an alkyl aromatic compound with carbon monoxide in the presence of a high boiling point carbonylation catalyst to form an alkyl aromatic aldehyde, wherein the catalyst has a first boiling point that is of at least 210° C. and is higher than a second boiling point of the aldehyde; and
   (b) separating said alkyl aromatic aldehyde from said carbonylation catalyst by selectively volatilizing said alkyl aromatic aldehyde.

5. The process according to claim 4, wherein said high boiling point carbonylation catalyst is selected from the group consisting of perfluoroalkyl sulfonic acids having 2 to 18 carbon atoms, perfluoroether sulfonic acids having 2 to 18 carbon atoms, $GaBr_3$, $GaCl_3$, $AlBr_3$, $AlCl_3$, $AlI_3$, $TaF_5$, $NbF_5$, and $NbBr_5$.

6. The process according to claim 5, wherein said high boiling point carbonylation catalyst is selected from the group consisting of $TaF_5$, $NbF_5$, and $NbBr_5$, and wherein said reaction takes place in the absence of added HF.

7. The process according to claim 5 wherein said high boiling point carbonylation catalyst is selected from the group consisting of perfluorohexane sulfonic acid, perfluorooctane sulfonic acid and perfluoroethoxyethane sulfonic acid.

8. The process according to claim 4, wherein said selective volatilization has a mean liquid residence time of up to 5 minutes and reaches a temperature of at least 90° C.

9. The process according to claim 8, wherein said selective volatilization reaches a temperature within the range from 100° C. to 300° C.

10. The process according to claim 8, wherein said selective volatilization is carried out in a wiped-film evaporator.

11. The process according to claim 8, wherein said selective volatilization uses flash distillation wherein temperatures reach at least 200° C. and the average liquid residence time is less than three minutes.

12. The process according to claim 4, wherein said reaction temperature is within the range of from 0° C. to 50° C.

13. The process according to claim 4, wherein said reacting step is carried out at a pressure within the range from 15 to 200 kg/cm² (gauge).

14. The process according to claim 4, wherein said reacting step is carried out under a carbon monoxide gas pressure from 1 to 100 kg/cm² (gauge).

15. The process according to claim 14, wherein said carbon monoxide gas pressure is within the range of from 2 to 25 kg/cm².

16. The process according to claim 4, which further comprises oxidizing said alkyl aromatic aldehyde after said separation step to aromatic acid.

17. The process according to claim 4, wherein said alkyl aromatic compound is selected from the group consisting of toluene, xylenes, pseudocumene, and mesitylene.

18. The process according to claim 17, wherein said alkyl aromatic compound is toluene and said aldehyde comprises p-tolualdehyde.

19. The process according to claim 18, which further comprises subjecting said p-tolualdehyde to oxidation to produce terephthalic acid.

20. The process according to claim 17, wherein said alkyl aromatic compound is a mixture of at least two of ortho-, meta-, and para-xylene and said aldehyde is a mixture of dimethylbenzaldehydes.

21. The process according to claim 20, which further comprises subjecting at least one of said dimethylbenzaldehydes to oxidation to produce trimellitic acid.

22. The process according to claim 17, wherein said alkyl aromatic compound is pseudocumene and said aldehyde is 2,4,5-trimethylbenzaldehyde.

23. The process according to claim 22, which further comprises oxidizing said 2,4,5-trimethylbenzaldehyde to pyromellitic acid and dehydrating to form pyromellitic dianhydride.

24. A process which comprises:
   reacting an alkyl aromatic compound with carbon monoxide in the presence of a carbonylation catalyst selected from the group consisting of perfluoroalkyl sulfonic acids having 2 to 18 carbon atoms, perfluoroether sulfonic acids having 2 to 18 carbon atoms, $GaBr_3$, $GaCl_3$, $TaF_5$, $NbF_5$, $NbBr_5$, and $BF_3 \cdot (ROH)_x$ wherein R represents $CH_3$ or H and X is a number within the range of from 0.2 to 2, to form an alkyl aromatic aldehyde wherein the catalyst has a first boiling point higher than a second boiling point of the aldehyde, with the proviso that when the catalyst is $TaF_5$, $NbF_5$, $NbBr_5$, then said reaction takes place in the absence of added HF; and separating the catalyst from the aldehyde by selective volatilization at a temperature of at least 200° C.

25. The process according to claim 24, which further comprises oxidizing said alkyl aromatic aldehyde to form an aromatic acid.

26. The process according to claim 24, wherein said reacting step takes place in the absence of added HF.

27. The process according to claim 24, wherein said catalyst is $BF_3 \cdot (ROH)_x$ and the reaction is carried out at a temperature within the range from 50° C. to 200° C.

28. The process according to claim 27, wherein R is $CH_3$.

29. A process which comprises:
   (a) reacting a mixture of ortho-, meta-, and para-xylenes with CO in the presence of a carbonylation catalyst to form a mixture of dimethylbenzaldehydes; wherein the catalyst has a first boiling point higher than a second boiling point of the aldehyde;
   (b) separating the catalyst from the mixture at a temperature of at least 200° C.,
   (c) oxidizing said mixture of dimethylbenzaldehydes to form trimellitic acid; and
   (d) dehydrating said trimellitic acid to form trimellitic anhydride.

30. A process which comprises:
   reacting an alkyl aromatic compound with carbon monoxide in the presence of a carbonylation catalyst selected from the group consisting of perfluoroalkyl sulfonic acids having 2 to 18 carbon atoms, perfluoroether sulfonic acids having 2 to 18 carbon atoms, $GaBr_3$, $GaCl_3$, $TaF_5$, $NbF_5$, $NbBr_5$, and $BF3·(ROH)_x$ wherein R represents $CH_3$ or H and X is a number within the range of from 0.2 to 2, to form an alkyl aromatic aldehyde wherein the catalyst has a first boiling point that is of at least 210° C. and is higher than a second boiling point of the aldehyde, with the proviso that when the catalyst is $TaF_5$, $NbF_5$, $NbBr_5$, then said reaction takes place in the absence of added HF.

31. A process which comprises:
(a) reacting a mixture of ortho-, meta-, and para-xylenes with CO in the presence of a carbonylation catalyst wherein the catalyst has a first boiling point that is at least 210° C. and is higher than a second boiling point of the aldehyde to form a mixture of dimethylbenzaldehydes;
(b) oxidizing said mixture of dimethylbenzaldehydes to form trimellitic acid; and (c) dehydrating said trimellitic acid to form trimellitic anhydride.

\* \* \* \* \*